(12) United States Patent
Wang et al.

(10) Patent No.: US 10,351,494 B1
(45) Date of Patent: Jul. 16, 2019

(54) SYSTEMS AND METHODS FOR REDUCING THE FORMATION OF IMPURITIES DURING 244BB DEHYDROCHLORINATION TO 1234YF

(71) Applicant: Honeywell International Inc., Morris Plains, NJ (US)

(72) Inventors: Haiyou Wang, Amherst, NY (US); Terris Yang, East Amherst, NY (US); Daniel C. Merkel, Orchard Park, NY (US); Haluk Kopkalli, Staten Island, NY (US); Gustavo Cerri, Parsippany, NJ (US); Yuon Chiu, Denville, NJ (US); Richard D. Horwath, Richmond, VA (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/864,730

(22) Filed: Jan. 8, 2018

(51) Int. Cl.
| | |
|---|---|
| *B01D 3/00* | (2006.01) |
| *B01D 3/36* | (2006.01) |
| *C07C 17/25* | (2006.01) |
| *C07C 21/18* | (2006.01) |
| *C07C 17/386* | (2006.01) |
| *C07C 17/395* | (2006.01) |

(52) U.S. Cl.
CPC .............. *C07C 17/25* (2013.01); *B01D 3/002* (2013.01); *B01D 3/36* (2013.01); *C07C 17/386* (2013.01); *C07C 17/395* (2013.01); *C07C 21/18* (2013.01)

(58) Field of Classification Search
CPC ..... C07C 17/383; C07C 17/395; C07C 17/25; C07C 21/18; C07C 19/10; Y02P 20/582
See application file for complete search history.

(56) References Cited

U.S. PATENT DOCUMENTS

| | | |
|---|---|---|
| 7,803,283 B2 | 9/2010 | Pham et al. |
| 8,058,486 B2 | 11/2011 | Merkel et al. |
| 8,697,923 B2 | 4/2014 | Smith et al. |
| 8,766,020 B2 | 7/2014 | Wang et al. |
| 8,975,454 B2 | 3/2015 | Merkel et al. |
| 9,296,670 B2 | 3/2016 | Wang et al. |
| 9,758,450 B2 | 9/2017 | Wang et al. |
| 2009/0256110 A1 | 10/2009 | Merkel et al. |
| 2010/0187088 A1 | 7/2010 | Merkel et al. |
| 2011/0031436 A1* | 2/2011 | Mahler .................. C07C 17/04 252/78.1 |
| 2012/0184785 A1 | 7/2012 | Cottrell et al. |
| 2015/0183698 A1* | 7/2015 | Merkel .................... B01J 27/10 570/136 |

FOREIGN PATENT DOCUMENTS

| | | |
|---|---|---|
| GB | 2547277 A | 8/2017 |
| WO | 2017013405 A1 | 1/2017 |
| WO | 2017066603 A1 | 4/2017 |

OTHER PUBLICATIONS

U.S. Appl. No. 62/416,206, filed Nov. 2, 2016, 17 pages.

* cited by examiner

*Primary Examiner* — Jafar F Parsa
(74) *Attorney, Agent, or Firm* — Faegre Baker Daniels LLP (57) ABSTRACT

The present disclosure provides various manufacturing processes for the production of 2,3,3,3-tetrafluoropropene (HFO-1234yf or 1234yf). Such methods may allow for the improved yields, more economical processes, and waste reduction in the production of 1234yf and subsequent processes.

19 Claims, 7 Drawing Sheets

SYSTEMS AND METHODS FOR REDUCING THE FORMATION OF IMPURITIES DURING 244BB DEHYDROCHLORINATION TO 1234YF

FIELD OF THE DISCLOSURE

This disclosure relates to manufacturing methods and systems for reducing the formation of impurities during the manufacture of HFO-1234yf. More specifically, this disclosure relates to methods for reducing the formation of impurities during dehydrochlorination of 2-chloro-1,1,1,2-tetrafluoropropane (HCFC-244bb or 244bb) to form 2,3,3,3-tetrafluoropropene (HFO-1234yf or 1234yf).

BACKGROUND

Hydrofluoroolefins (HFOs), such as tetrafluoropropenes are known effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for the applications mentioned above.

Hydrofluoroolefins (HFOs) having zero ozone depletion and low global warming potential have been identified as potentially filling this need. However, the toxicity, boiling point, and other physical properties of such chemicals vary greatly from isomer to isomer. One HFO having valuable properties is 2,3,3,3-tetrafluoropropene (HFO-1234yf or 1234yf).

HFO-1234yf has been shown to be a low global warming compound with low toxicity and, thus, can meet increasingly stringent requirements for refrigerants in mobile air conditioning. Accordingly, compositions containing HFO-1234yf are among the materials being developed for use in many of the aforementioned applications.

Various methods are known for producing HFO-1234yf, such as those described in U.S. Pat. No. 8,058,486, entitled INTEGRATED PROCESS TO PRODUCE 2,3,3,3-TETRAFLUOROPROPENE issued on Nov. 15, 2011, U.S. Pat. No. 8,975,454, entitled PROCESS FOR PRODUCING 2,3,3,3-TETRAFLUOROPROPENE issued on Mar. 10, 2015, and U.S. Pat. No. 8,766,020, entitled PROCESS FOR PRODUCING 2,3,3,3-TETRAFLUOROPROPENE issued on Jul. 1, 2014, all of which are herein incorporated by reference in their entirety.

SUMMARY

The present disclosure provides various manufacturing processes for the production of 2,3,3,3-tetrafluoropropene (HFO-1234yf or 1234yf). Such methods may allow for the improved yields, more economical processes, and waste reduction in the production of 1234yf and subsequent processes.

According to various aspects of this disclosure, methods of manufacturing 2,3,3,3-tetrafluoropropene (HFO-1234yf) may include providing a feed comprising 2-chloro-1,1,1,2-tetrafluoropropane (HCFC-244bb) and at least one heavy organic impurity having a boiling point higher than about 15° C., removing the at least one impurity from the feed until the feed contains less than 200 ppm of the at least one impurity, and dehydrochlorinating the HCFC-244bb in the feed to form a product stream containing HFO-1234yf. In certain embodiments, it's preferable to remove the at least one impurity from the feed until the feed contains less than 100 ppm of the at least one impurity, and more preferable to remove the at least one impurity from the feed until the feed contains less than 50 ppm of the at least one impurity.

In some embodiments, the at least one impurity comprises at least one of 1,1,1,3-tetrachloropropane (HCFC-253fb), 1,1,1,3,3-pentafluoropropane (HFC-245fa), chlorohexafluorobutene (HFO-1326 isomer), hexafluorobutene (HFO-1336 isomer), pentafluorobutene (HFO-1345 isomer), heptafluorobutene (HFO-1327 isomer), 2,3-dichloro-1,1,1,2-tetrafluoropropane (HFC-234bb), chlorotetrafluoropropenes (HCFO-1224 isomers), tetrafluorohexane (HFC-5-11-4 isomer), tetrafluoropropane (HFC-254 isomer), chlorohexafluorobutane (HFC-346 isomer), octafluoropentane (HFC-458 isomer), chlorotrifluoropropene (HCFO-1233 isomer), (E)-1-chloro-3,3,3-trifluoropropene (HCFO-1233zd(E)), 2-chloro-1,1,1,3,3-pentafluoropropane (HCFC-235da), octafluorohexene, 3-chloro-1,1,1,2-tetrafluoropropane (HFC-244eb), 2,2-dichloro-1,1,1-trifluoroethane (HCFC-123), (Z)-1-chloro-3,3,3-trifluoropropene (HCFO-1233zd(Z)), $C_6H_2F_{10}$ isomer, $C_6H_2F_8$ isomer, $C_6H_4F_8$ isomer, decafluorobutane ($C_4F_{10}$), $C_6H_3F_7$ isomer, $C_6H_3F_9$ isomer, dichlorodifluoropropene (HCFO-1232 isomers), dichlorotrifluoropropene (HCFO-1223 isomers), dichlorotetrafluoropropane (HCFC-234 isomers), dichlorotrifluoropropane (HCFC-243 isomer), trichlorotrifluoropropane (HCFC-233 isomers), $C_6H_3Cl_2F_7$ isomer, trichlorodifluoropropane (HCFC-242 isomers), C8H3F7 isomer, tars, or combinations thereof.

Various methods may further include treating the product stream containing HFO-1234yf with at least one of a column containing HCl, a column containing water, a column containing a caustic solution, a scrubber, a dryer, a distillation column, or a combination thereof.

Some methods of manufacturing 2,3,3,3-tetrafluoropropene (HFO-1234yf) may also include providing a feed comprising 2-chloro-1,1,1,2-tetrafluoropropane (HCFC-244bb) and at least one impurity, dehydrochlorinating the HCFC-244bb in the feed to form a product stream containing HFO-1234yf, controlling the formation of 1140, 1243zf, or combinations thereof at or below a predetermined threshold. In various embodiments, this may include removing 1,1,1,3-tetrachloropropane (HCFC-253fb) before dehydrochlorinating the HCFC-244bb in the feed.

BRIEF DESCRIPTION OF THE DRAWINGS

The above mentioned and other features and objects of this disclosure, and the manner of attaining them, will become more apparent and the disclosure itself will be better understood by reference to the following description of exemplary embodiments of the disclosure taken in conjunction with the accompanying drawings, wherein.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplification set out herein illustrates exemplary embodiments of the disclosure, in various forms, and such exemplifications are not to be construed as limiting the scope of the disclosure in any manner.

DETAILED DESCRIPTION

As briefly described above, this disclosure provides various methods and systems for the manufacture of 2,3,3,3-tetrafluoropropene (HFO-1234yf or 1234yf). The manufacture of HFO-1234yf from 1,1,2,3-tetrachloropropene (TCP) and hydrogen fluoride can be generalized in a three step process.

Step 1 can be understood as producing 2-chloro-3,3,3-trifluoropropene (HCFO-1233xf) from 1,1,2,3-tetrachloropropene (1230xa) in a vapor phase reactor according to the following reaction scheme:

1,1,2,3-tetrachloropropene
(HCC-1230xa)

2-chloro-3,3,3-trifluoropropene
(HCFO-1233xf)

Step 2 can be understood as producing 2-chloro-1,1,1,2-tetrafluoropropane (HCFC-244bb) from 2-chloro-3,3,3-trifluoropropene (HCFO-1233xf) in a reactor, such as a liquid phase reactor, according to the following reaction scheme:

2-chloro-3,3,3-trifluoropropene
(HCFO-1233xf)

2-chloro-1,1,1,2-tetrafluoropropane
(HCFC-244bb)

Step 3 can be understood as producing 2,3,3,3-tetrafluoropropene (HFO-1234yf) from 2-chloro-1,1,1,2-tetrafluoropropane (HCFC-244bb) in a reactor, such as a vapor phase reactor according to the following reaction scheme:

2-chloro-1,1,1,2-tetrafluoropropane
(HCFC-244bb)

2,3,3,3-tetrafluoropropene
(HFO-1234yf)

Not wishing to be bound by or to any particular theory of operation, certain aspects of the present invention are based on the observation and understanding that, during certain dehydrochlorination reactions of certain dehydrochlorination starting materials, such as 2-chloro-1,1,1,2-tetrafluoropropane (HCFC-244bb) to produce 2,3,3,3-tetrafluoropropene (HFO-1234yf) according to Step 3 above, the presence of certain impurities has been found to be detrimental and disadvantageous.

For example, the presence of 3-chloro-1,1,1-trifluoropropane (HCFC-253fb or 253fb) in the reactor for Step 3 may result in the formation and/or presence of elevated levels of both 3,3,3-trifluoropropene (HFO-1243zf or 1243zf) and vinyl chloride (1140), which may be subsequently found in 1234yf crude product. The presence of the 1243zf and 1140 impurities can result in extra yield loss during final purification steps and is thus undesired due to the difficulty of separating 1243zf and 1140 from 1234yf.

Also, the presence of high boilers and tars (which are long-chain halogenated hydrocarbons) formed as side-reactions in the reactor of Step 3 appears to either cause excessive coking of the Step 3 reactor or contribute to it, resulting in premature deactivation of the reactor. Non-limiting examples of high boilers include, but are not limited to, $C_4F_{10}$, $C_5H_2F_{10}$ isomers, various tetrafluorohexane isomers, $C_6H_3F_7$ isomers, $C_6H_3Cl_2F_7$ isomers, $C_6H_2F_8$ isomers, $C_6H_4F_8$ isomers, $C_6H_3F_8$ isomers, various octafluorohexene isomers, and $C_8H_3F_7$ isomers. These high boilers may further react to form tar, which can be condensed to form a dark brown or black viscous liquid upon cooling.

Thus, for the feed to the Step 3 reactors, the reduction of certain impurities and/or reduction and separations of tars, high boilers, and precursors of these materials may allow for a more economical process, improved uptime, higher yield, and may allow for the improved use of the metallic surface of the reactor. In turn, this may also allow for the process to run at milder conditions, which may also help prevent the production of undesirable byproducts.

The embodiments disclosed below are not intended to be exhaustive or limit the disclosure to the precise form disclosed in the following detailed description. Rather, the embodiments are chosen and described so that others skilled in the art may utilize their teachings.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

Figure 1A:
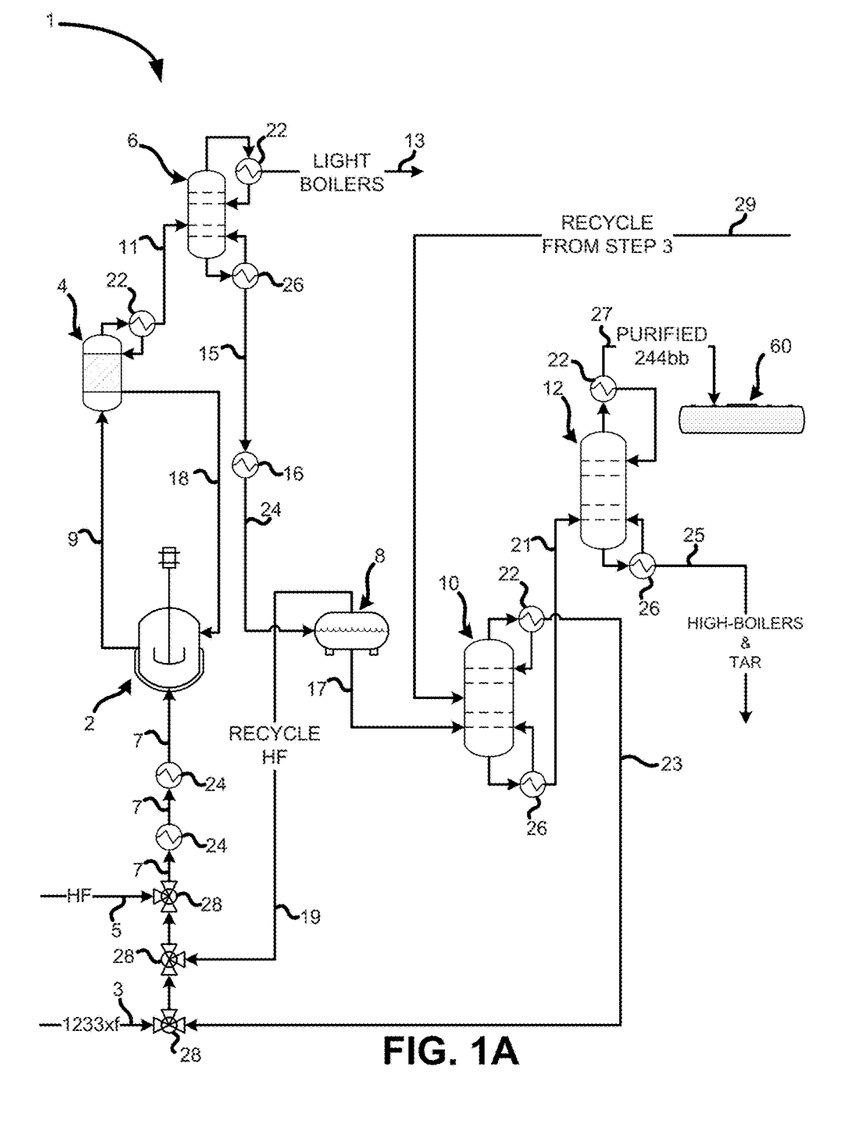
FIG. 1A is a process flow diagram showing an exemplary portion of a manufacturing process of 2,3,3,3-tetrafluoropropene (HFO-1234yf)

FIG. 1A is process flow diagram illustrating exemplary manufacturing process flow 1 according to various embodiments. HF feed 5 and 1233xf feed 3 (from Step 1) may be combined, for example, with any pipe or vessel, such as combination flow valves 28 and may be heated by heat exchangers 24 and then fed as stream 7 to reactor 2. In reactor 2, which may be and is shown in FIG. 1A as a liquid phase reactor, HCFC-244bb is produced as briefly described above as Step 2. After the reaction of Step 2 takes place in reactor 2, the crude HCFC-244bb product stream 9 is sent to catalyst stripper column 4, where catalysts are separated and are returned to reactor 2 in return stream 18. After processing in catalyst stripper column 4 and heat exchanger 22, the stripped crude HCFC-244bb product stream 11 is sent to lights distillation column 6. In lights distillation column, the light boilers are distilled off as lights overhead stream 13, while the lights bottoms stream 15 may be cooled by heat exchanger 16 and may be sent to phase separator 8 via stream 24, where HF is separated from the lights bottoms stream 15, which contains HCFC-244bb. The HF phase may then be recycled back to the Step 2 reactor as recycle HF stream 19 and the liquid stream 17 containing HCFC-244bb may be sent to one or more distillation columns.

FIG. 1A illustrates liquid stream 17 being sent first to distillation column 10, which in this embodiment is exemplified as an azeotropic distillation column. In other embodiments, distillation column 10 may include non-azeoptropic distillation.

In azeotropic distillation column 10, HCFO-1233xf may be removed from the HCFC-244bb liquid stream using azeotropic distillation. As used herein, the term azeotropic distillation is used in the broad sense to include distillation processes that include one or more azeotrope or azeotrope-like mixtures of two or more fluids. To this end, a third stream, such as unreacted reagents and/or byproducts from Step 3, may be provided by recycle stream 29 to form an azeotrope or azeotropic composition, which is then isolated from the composition. More specifically, the presence of a third component (e.g., HF) may form a ternary azeotrope and/or binary azeotropes with HCFO-1233xf, and/or HCFC-244bb. Various azeotropes may be separated from the solution using standard separation means, such as distillation in azeotropic distillation column 10, such that a significant portion of the HCFC-244bb remains in solution in bottoms 21.

In various embodiments of this disclosure, a composition which comprises effective amounts of HF, light organics, heavy organics, or combinations thereof to form an azeotropic or azeotrope-like composition is provided. As used herein, the term "effective amount" is an amount of each component which, when combined with the other component, results in the formation of an azeotrope or azeotrope-like mixture. As used herein, the terms "heteroazeotrope" and "heterogeneous azeotrope" include an azeotrope-like compositions comprising a vapor phase existing concurrently with two liquid phases.

Such azeotropes and methods of azeotropic separation or distillation may further include those disclosed in U.S. Pat. No. 7,803,283, and U.S. Published Application Nos. 2010/0187088 and 2009/0256110, the contents of each of which are all incorporated herein by reference.

Azeotropic column bottoms 21 may then be isolated as purified HCFC-244bb in heavies distillation column 12 that may be substantially free of 253fb, and other heavy impurities, shown as purified overhead HCFC-244bb stream 27, which may be sent for further processing (e.g., Step 3) and/or stored in tank 60. Overhead stream 23 from column may then be recycled back to be reused in Step 2 in reactor 2 and may be combined with feed stream 7, for example, with a pipe or vessel, such as with combination flow valves 28.

Finally, bottoms 25 of heavies distillation column 12, which may contain enriched 253fb as well as tars and/or other heavy boilers, may then be collected, subjected to additional recovery to improve yield and/or disposed of. As used herein, the term "heavy boilers" may include organic compositions that have a boiling point higher than 244bb, which has a normal boiling point of about 14-15° C. For example, in some embodiments, heavy organics may have a boiling point above about 15° C. Heavy organics may include HCFC-253fb, $C_4F_{10}$, $C_5H_2F_{10}$ isomers, various tetrafluorohexane isomers, $C_6H_3F_7$ isomers, $C_6H_3Cl_2F_7$ isomers, $C_6H_2F_8$ isomers, $C_6H_4F_8$ isomers, $C_6H_3F_9$ isomers, various octafluorohexene isomers, $C_8H_3F_7$ isomers, tars, or combinations thereof.

Figure 1B:
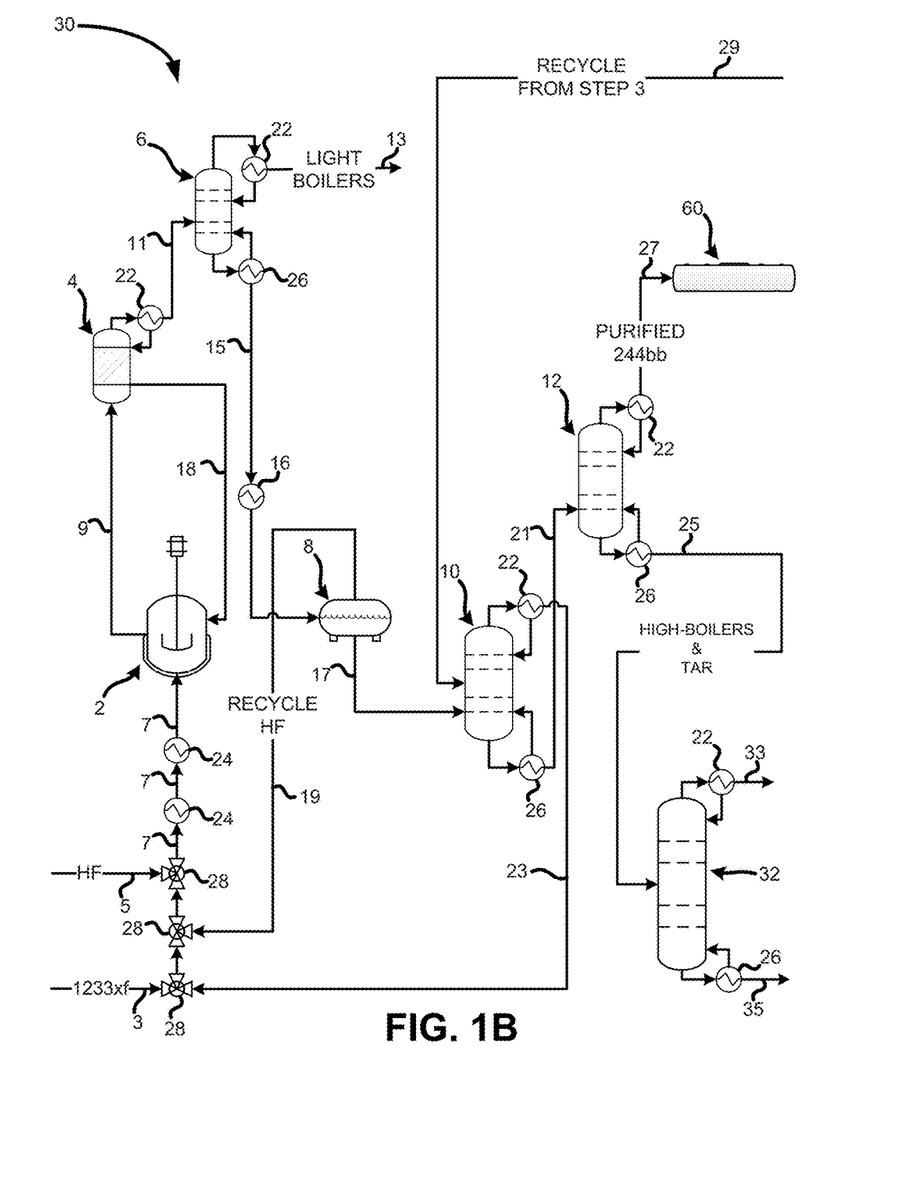
FIG. 1B is a process flow diagram similar to the process flow depicted in FIG. 1A that additionally includes a third distillation column in series.

Thus, in some embodiments, such as the process flow diagram depicted in FIGS. 1A and 1B, the impurities removed may include at least one of 1-chloro-3,3,3-trifluoropropane (HCFC-253fb), 1,1,1,3,3-pentafluoropropane (HFC-245fa), chlorohexafluorobutene (HFO-1326 isomer), hexafluorobutene (HFO-1336 isomer), pentafluorobutene (HFO-1345 isomer), heptafluorobutene (HFO-1327 isomer), 2,3-dichloro-1,1,1,2-tetrafluoropropane (HFC-234bb), chlorotetrafluoropropenes (HCFO-1224 isomers), tetrafluorohexane (HFC-5-11-4 isomer), tetrafluoropropane (HFC-254 isomer), chlorohexafluorobutane (HFC-346 isomer), octafluoropentane (HFC-458 isomer), chlorotrifluoropropene (HCFO-1233 isomer), (E)-1-chloro-3,3,3-trifluoropropene (HCFO-1233zd(E)), 2-chloro-1,1,1,3,3-pentafluoropropane (HCFC-235da), octafluorohexene, 3-chloro-1,1,1,2-tetrafluoropropane (HFC-244eb), 2,2-dichloro-1,1,1-trifluoroethane (HCFC-123), (Z)-1-chloro-3,3,3-trifluoropropene (HCFO-1233zd(Z)), $C_5H_2F_{10}$ isomer, $C_6H_2F_8$ isomer, $C_6H_4F_8$ isomer, decafluorobutane ($C_4F_{10}$), $C_6H_3F_7$ isomer, $C_6H_3F_9$ isomer, dichlorodifluoropropene (HCFO-1232 isomers), dichlorotrifluoropropene (HCFO-1223 isomers), dichlorotetrafluoropropane (HCFC-234 isomers), dichlorotrifluoropropane (HCFC-243 isomer), trichlorotrifluoropropane (HCFC-233 isomers), $C_6H_3Cl_2F_7$ isomer, trichlorodifluoropropane (HCFC-242 isomers), $C_8H_3F_7$ isomer, tars, or combinations thereof.

In some embodiments, such as process flow 30 depicted in FIG. 1B, which includes many aspects which are similar or identical to that of FIG. 1A, bottoms 25 of heavies distillation column 12 may be further separated, such as with distillation column 32. In some embodiments, heavies recovery distillation column 32 may further separate the high-boilers and tar from heavies distillation column 12 into overhead 33 and bottoms 35. In various embodiments, heavies recovery distillation column 32 may operate by batch distillation and in other embodiments, distillation column 32 may operate by continuous distillation. Also, in some embodiments, the purified 244bb or partially purified 244bb may be stored in a storage container, such as storage container 60.

Figure 1C:
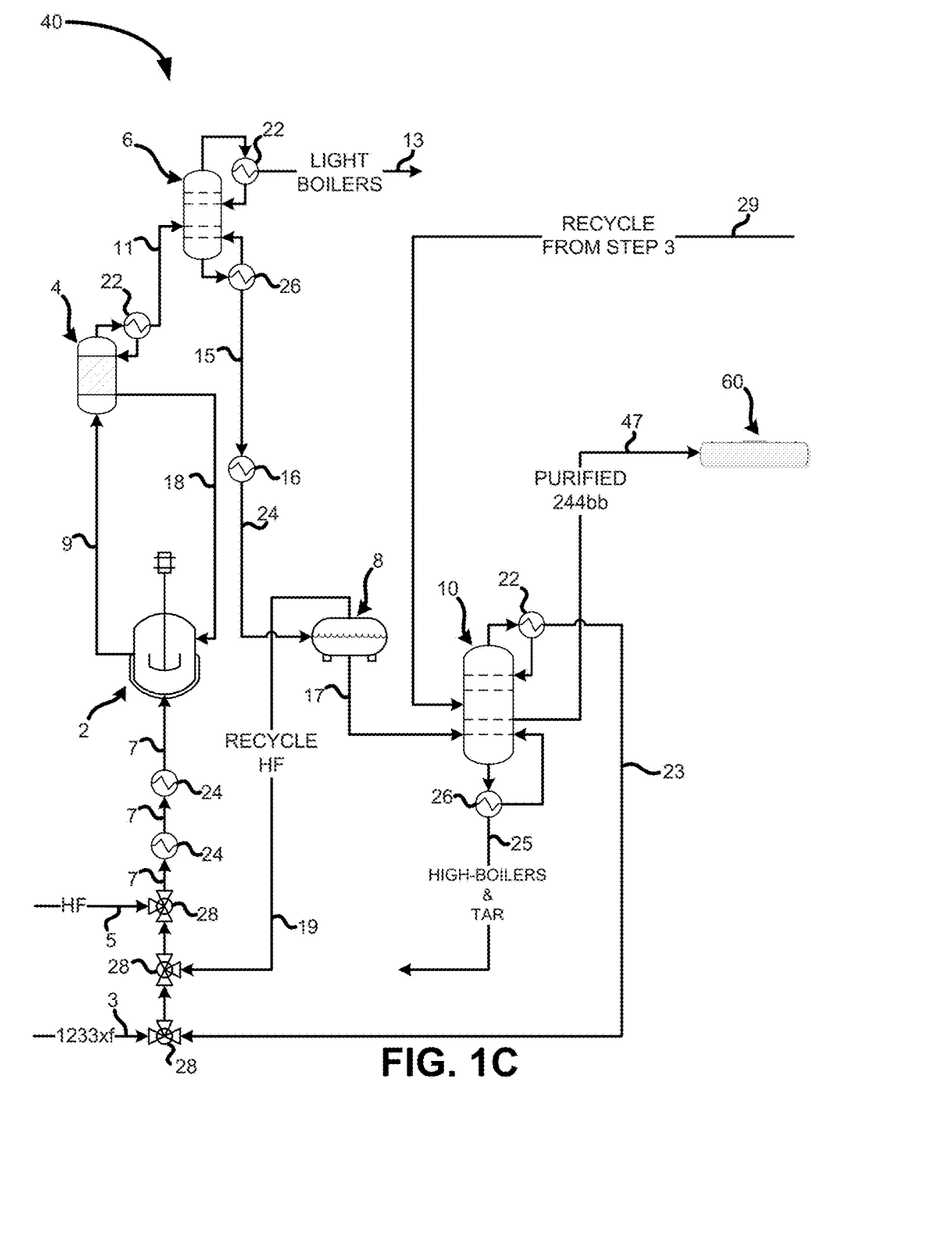
FIG. 1C is a process flow diagram similar to the process flow depicted in FIG. 1A showing an exemplary portion of a manufacturing process of 2,3,3,3-tetrafluoropropene (HFO-1234yf) using a side-draw from a distillation column.

In some embodiments, such as process flow 40 depicted in FIG. 10, which includes many aspects which are similar or identical to that of FIG. 1A, illustrates the separation of purified 244bb using a side-draw 47 off of distillation column 10. In some embodiments, the use of a side-draw may be beneficial due to the separation differences within the various trays of distillation column 10 due to the vapor pressure differences between the high-boilers and tar and the purified 244bb.

Figure 2:
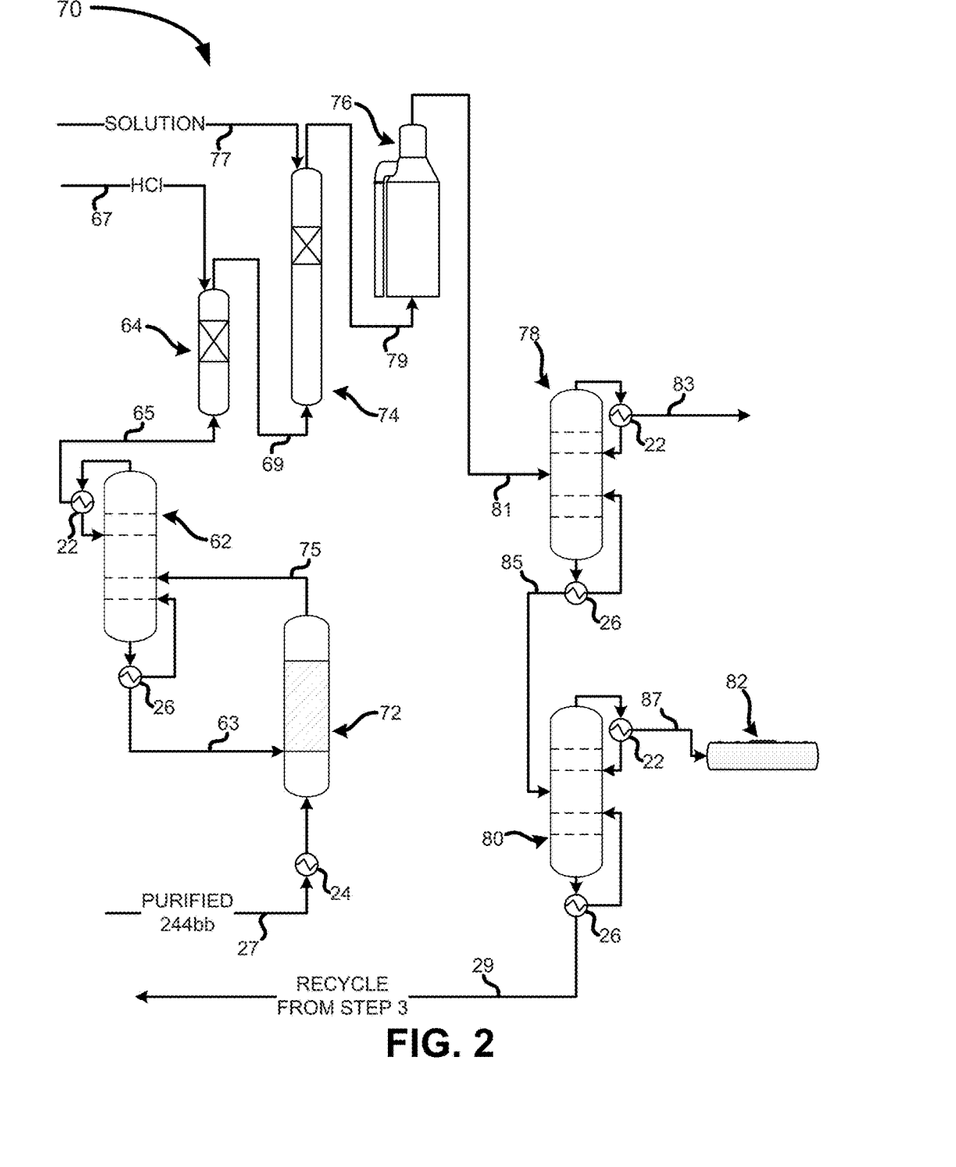
FIG. 2 is a process flow diagram depicting Step 3 of an exemplary process of manufacturing HFO-1234yf.

FIG. 2 illustrates process flow diagram 70 showing the production of 1234yf from a feed containing a purified 244bb and at least one impurity. Process flow diagram 70 of FIG. 2 includes an input stream 27 containing HCFC-244bb, which may contain the at least one of the aforementioned impurities, as exemplified in the description of FIGS. 1A and 1B.

The composition containing HCFC-244bb and at least one of the aforementioned impurities may then be heated by heat exchanger 24 and sent to dehydrochlorinating reactor 72 to produce 1234yf (Step 3 as briefly described above). The reacted product stream 75 containing the 1234yf may then be sent to recycle column 62, where bottoms 63 may be recycled back to reactor 72 and/or back to Step 2 azeotropic distillation column 10 as stream no. 29 in FIG. 1A and FIG. 1B, and overhead 65 may be sent to be scrubbed with HCl stream 67 in HCl column 64. The HCl scrubbed stream 69 may then scrubbed with solution stream 77 in scrubber 74. The solution stream 77 is not particularly limited and may be water or a solution, such as a caustic solution or an acidic solution, such as a solution containing sulfuric acid. The scrubbed product stream 79 may then be sent to drier 76 containing an acid, such as concentrated sulfuric acid or a solid desiccant or mixture of solid desiccants or a combination of concentrated sulfuric acid and desiccant(s) to remove any scrubbing solution/moisture that may remain. A precooling step may be incorporated between scrubber 74 and drier 76 to differentially condense water vapors to conserve drying agent in dryer 76.

The dried product stream 81 may then be distilled in lights distillation column 78, where overhead lights stream 83 is passed through heat exchanger 22 and recycled or removed. Lights bottoms stream 85 may be heated or cooled via heat exchanger 26 and may be further distilled in product distillation column 80. Purified 1234yf stream 87 may be processed through heat exchanger 22 and may be stored in container 82 and/or recycled. Product bottoms stream 29 may be heated with heat exchanger 26 and may be recycled back into product distillation column 80 and/or may be removed for disposal.

In some embodiments, the formation of 1140, 1243zf, or combinations thereof may be controlled below a predetermined threshold, for example in the effluent of the reactor in Step 3 (shown as dehydrochlorinating reactor 72 in FIG. 2). In various embodiments, the formation of 1140, 1243zf, and combinations thereof may be controlled by the selective removal of their precursors, such as 253fb.

Without being limited to any particular theory, it is believed that increased amounts of 253fb may lead to increased amounts of 1243zf, 1140, and combinations thereof, including other side reactants. It has been found that increased levels of 253fb can lead to increased undesirable side reactions that can negatively affect yield, such as the formation of 1140 and 1243zf according to the following reaction Schemes I and II:

Thus, in various embodiments the amount of 1243zf, 1140, and combinations thereof may be controlled to be below a predetermined threshold. For example, limiting the amount of HCFC-253fb with any of the aforementioned separation processes, such as distillation may help to control the amount of HFO-1243zf and 1140 produced. For example, in some embodiments, HCFC-253fb may be removed via distillation or a series of distillation, such as is shown in FIGS. 1A and 1B.

For example, in some embodiments, the amount of HCFC-253fb may be reduced to levels below about 200 ppm, to levels below about 100 ppm, to levels below about 50 ppm, or to levels below about 30 ppm. This in turn, may help to limit the formation of HFO-1243zf and 1140 because the precursor to these aforementioned compounds (as shown in Schemes I and II) is not available.

For example, in some embodiments, by limiting the presence of HCFC-253fb, the formation of 1140 may be controlled to an amount less than about 200 ppm, less than about 100 ppm, less than about 50 ppm, or less than about 30 ppm.

Similarly, in some embodiments, the formation of 1243zf may also be controlled by limiting the presence of HCFC-253fb. Thus, the formation of HFO-1243zf controlled to (minimized to) levels of less than about 200 ppm, less than about 100 ppm, less than about 80 ppm, or less than about 50 ppm.

Also, in some embodiments the combination of 1140 and 1243zf may be controlled to an amount less than about 300 ppm, less than about 200 ppm, less than about 100 ppm, or less than 80 ppm. For example, in various embodiments, controlling the formation of 1140 and 1243zf can be accomplished by removal of 253fb prior to performing Step 3, for example, by removing 253fb in the feed stream to Step 3 so the feed stream has an amount of 253fb less than about 200 ppm, less than about 100 ppm, less than about 50 ppm, or less than 30 ppm.

Figure 3:
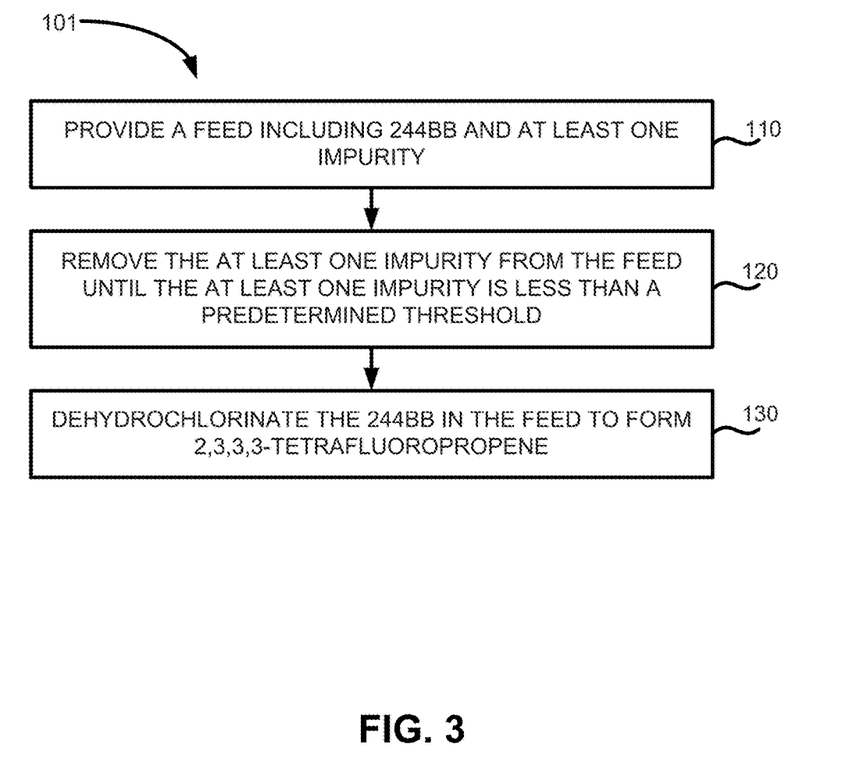
FIG. 3 illustrates a portion of method of manufacture of HFO-1234yf while controlling the formation of 1140, 1243zf, and combinations thereof according to various embodiments.
Figure 4:
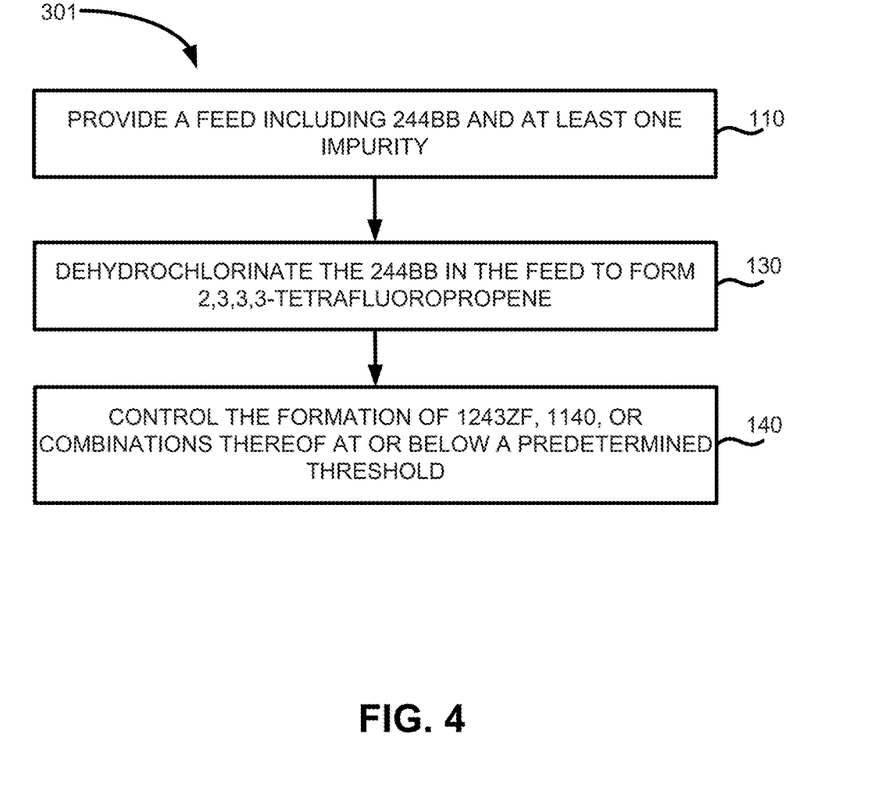
FIG. 4 illustrates a method of manufacture of HFO-1234yf according to various embodiments.

Thus, methods of manufacturing 2,3,3,3-tetrafluoropropene may include the methods depicted in FIGS. 3 and 4. FIG. 3 illustrates method 101 of manufacturing 2,3,3,3-tetrafluoropropene, which may include providing a feed comprising 244bb and at least one impurity (step 110), removing the at least one impurity from the feed until the feed contains less than a predetermined threshold (e.g., less than about 200 ppm, less than about 100 ppm, less than about 50 ppm, and less than about 30 ppm) of the at least one impurity (step 120), and dehydrochlorinating the 244bb in the feed to form a product stream containing 1234yf (step 130).

FIG. 4 illustrates another method of manufacturing 2,3,3,3-tetrafluoropropene according to various embodiments. Method 301 may include steps 110 and steps 130 as described above. Method 301 may also include the step of controlling the formation of 1243zf, 1140, or combinations thereof below a predetermined threshold (step 140). In various embodiments, this may be accomplished through the removal of 253fb to a predetermined threshold.

Dehydrochlorination of HCFC-244bb may be carried out at a temperature range of 200° C. to 800° C., preferably from 300° C. to 600° C., and more preferably from 425° C. to 525° C., and at a pressure range of 0 to 300 psig, preferably from 5 to 200 psig, and more preferably from 20 to 100 psig. Residence time of the HCFC-244bb in reactor may range from about 1 second to about 320 seconds, however, longer or shorter times can be used.

As described above and shown in the various process flow diagrams, the removing of the at least one impurity may include the use of one or more various separation processes or manufacture processes. Exemplary processes include decanting, centrifuging, liquid-liquid extraction, distilling, flash distilling, partial vaporization, partial condensing, or combinations thereof. The separation processes may be performed on a continuous or batch process, for example in a multi-stage distillation tower which may be operated in batch or continuous mode. In some embodiments, the separation of the impurity can be accomplished with a side draw from the distillation column.

In some embodiments, the product stream containing 1234yf may be further processed. For example, in some embodiments some separated streams or further processed streams may be recycled to improve the overall yield of the process. For example, in some embodiments, unreacted 2-chloro-1,1,1,2-tetrafluoropropane may be recycled after dehydrochlorination by using a recycle column.

The further processing is not particularly limited and may include various treatments with multiple unit operations, such as an HCl recovery column, a caustic scrubber, a sulfuric acid drying column, and product purification columns, etc.

EXAMPLES

Example 1

The goal of the examples below was to demonstrate the feasibility of removing 253fb and other high boilers from 244bb crude product. Batch distillation was run in 15 tray glass Oldershaw batch column at a RR (Reflux Ratio) of 1:1. About 3.8 lbs. of 244bb crude was charged to the glass still. Four distillate cuts were taken during distillation and a dark, almost black residue remained in the reboiler after distillation. As shown in Table 1, compared to those in initial 244bb crude, 253fb and other heavy components get significantly reduced in distillates while they got enriched in reboiler (Compared to 145 ppm 253fb in initial 244bb crude, Cuts 1-3 contained less than 5 ppm of 253fb, Cut 4 contained 89.0 ppm 253fb, while the reboiler residue had 9551 ppm 253fb; compared to about 1.25% other heavy components, Cuts 1-3 contained less than 0.65% of other heavy components, Cut 4 contained about 1.23% other heavy components, while the reboiler residue had 21.66% other heavy components). These results indicate 253fb and other heavy components can be effectively reduced via distillation.

TABLE 1

| Description | Weight, g | Organic composition, GC area % | | | | |
| --- | --- | --- | --- | --- | --- | --- |
| | | Other lights | 1233xf | 244bb | 253fb | Other heavies |
| 244bb crude | 1747.9 | 0.0302 | 0.8229 | 97.8814 | 0.0145 | 1.251 |
| Cut no. 1 | 468.5 | 0.0217 | 0.9415 | 98.6046 | 0.0001 | 0.431 |
| Cut no. 2 | 370.4 | 0.0155 | 0.8817 | 98.5612 | 0.0003 | 0.5413 |
| Cut no. 3 | 343.1 | 0.0166 | 0.8210 | 98.5187 | 0.0003 | 0.6434 |
| Cut no. 4 | 437.1 | 0.0287 | 0.6708 | 98.0584 | 0.0089 | 1.2332 |
| Residue | 22.5 | 0.3007 | 0.3500 | 76.7347 | 0.9551 | 21.6595 |

In table 1 above, the "other lights" refer to components having boiling points lower than that of 244bb that does not include 1233xf (for example, non-limiting examples include tetrafluoropropene (HFO-1234 isomers, pentafluoropropene (HFO-1225 isomers), heptafluorobutenes, and 2-chloro-1,1,1,2-tetrafluoroethane (HCFC-124)).

In Table 1 above, the "other heavies" refers to components having boiling points higher than that of 244bb besides 253fb (non-limiting examples include 1,1,1,3,3-pentafluoropropane (HFC-245fa), chlorohexafluorobutene (HFO-1326 isomer), hexafluorobutene (HFO-1336 isomer), pentafluorobutene (HFO-1345 isomer), heptafluorobutene (HFO-1327 isomer), 2,3-dichloro-1,1,1,2-tetrafluoropropane (HFC-234bb), chlorotetrafluoropropenes (HCFO-1224 isomers), tetrafluorohexane (HFC-5-11-4 isomer), tetrafluoropropane (HFC-254 isomer), chlorohexafluorobutane (HFC-346 isomer), octafluoropentane (HFC-458 isomer), chlorotrifluoropropene (HCFO-1233 isomer), (E)-1-chloro-3,3,3-trifluoropropene (HCFO-1233zd(E)), 2-chloro-1,1,1,3,3-pentafluoropropane (HCFC-235da), octafluorohexene, 3-chloro-1,1,1,2-tetrafluoropropane (HFC-244eb), 2,2-dichloro-1,1,1-trifluoroethane (HCFC-123), (Z)-1-chloro-3,3,3-trifluoropropene (HCFO-1233zd(Z)), $C_6H_2F_{10}$ isomer, $C_6H_2F_8$ isomer, $C_6H_4F_8$ isomer, decafluorobutane ($C_4F_{10}$), $C_6H_3F_7$ isomer, $C_6H_3F_8$ isomer, dichlorodifluoropropene (HCFO-1232 isomers), dichlorotrifluoropropene (HCFO-1223 isomers), dichlorotetrafluoropropane (HCFC-234 isomers), dichlorotrifluoropropane (HCFC-243 isomer), trichlorotrifluoropropane (HCFC-233 isomers), $C_6H_3Cl_2F_7$ isomer, trichlorodifluoropropane (HCFC-242 isomers), $C_8H_3F_7$ isomer, and tars).

Example 2

The goal of the examples below was to demonstrate the feasibility of removing high boilers from 244bb crude product. Batch distillation was run in a distillation column consisting of a 10 gallon jacketed reboiler, 2 inch ID by 8 feet high column packed with Monel Pro-Pak® column packing, and a shell and tube condenser. The column had about 35-40 theoretical plates. The distillation column was equipped with temperature, pressure, and differential pressure transmitters. The distillate rate was measured using a coriolis flow meter.

About 98 lbs. of 244bb crude was charged to the S1 distillation column. Its composition is presented in Table 2. The distillation was then started and run at a pressure of about 12-15 psig. 92 lbs. of purified 244bb distillate was collected. The 244bb distillate was analyzed and its composition is presented in Table 2. As shown in Table 2, 253fb was completely removed after distillation while the total amount of other heavy components was significantly reduced.

About 3 lbs. of black reboiler residue was drained from the reboiler after the completion of distillation. The 92 lbs. of purified 244bb distillate was subsequently used as the feed stock for dehydrochlorination reaction experiments.

TABLE 2

| Description | Weight, lb. | Organic composition, GC area % | | | | |
| --- | --- | --- | --- | --- | --- | --- |
| | | Other lights | 1233xf | 244bb | 253fb | Other heavies |
| 244bb crude | 98 | 1.3474 | 2.8190 | 94.6978 | 0.1100 | 1.0258 |
| 244bb distillate | 92 | 0.9698 | 2.8991 | 95.6815 | 0.0000 | 0.4496 |

In Table 2 above, the "other lights" refers to components having boiling points lower than that of 244bb besides 1233xf (non-limiting examples include tetrafluoropropene (HFO-1234 isomers, pentafluoropropene (HFO-1225 isomers), heptafluorobutenes, and 2-chloro-1,1,1,2-tetrafluoroethane (HCFC-124)).

In Table 2 above, the "other heavies" refers to components having boiling points higher than that of 244bb besides 253fb (non-limiting examples include 1,1,1,3,3-pentafluoropropane (HFC-245fa), chlorohexafluorobutene (HFO-1326 isomer), hexafluorobutene (HFO-1336 isomer), pentafluorobutene (HFO-1345 isomer), heptafluorobutene (HFO-1327 isomer), 2,3-dichloro-1,1,1,2-tetrafluoropropane (HFC-234bb), chlorotetrafluoropropenes (HCFO-1224 isomers), tetrafluorohexane (HFC-5-11-4 isomer), tetrafluoropropane (HFC-254 isomer), chlorohexafluorobutane (HFC-346 isomer), octafluoropentane (HFC-458 isomer), chlorotrifluoropropene (HCFO-1233 isomer), (E)-1-chloro-3,3,3-trifluoropropene (HCFO-1233zd(E)), 2-chloro-1,1,1,3,3-pentafluoropropane (HCFC-235da), octafluorohexene, 3-chloro-1,1,1,2-tetrafluoropropane (HFC-244eb), 2,2-dichloro-1,1,1-trifluoroethane (HCFC-123), (Z)-1-chloro-3,3,3-trifluoropropene (HCFO-1233zd(Z)), $C_5H_2F_{10}$ isomer, $C_6H_2F_8$ isomer, $C_6H_4F_8$ isomer, decafluorobutane ($C_4F_{10}$), $C_6H_3F_7$ isomer, $C_6H_3F_8$ isomer, dichlorodifluoropropene (HCFO-1232 isomers), dichlorotrifluoropropene (HCFO-1223 isomers), dichlorotetrafluoropropane (HCFC-234 isomers), dichlorotrifluoropropane (HCFC-243 isomer), trichlorotrifluoropropane (HCFC-233 isomers), $C_6H_3Cl_2F_7$ isomer, trichlorodifluoropropane (HCFC-242 isomers), $C_8H_3F_7$ isomer, and tars).

Example 3

Two 11.5" Inconel® 625 tubes (¾" OD with 0.035" wall thickness) were used as the reactor for Step 3 reaction (Dehydrochlorination of HCFC-244bb to produce HFO-1234yf) and installed in parallel in an electric box oven. With $N_2$ purge, the tube reactors were heated to a given temperature, then starting materials containing HCFC-244bb and other impurities were fed into each tube reactor with each feed controlled independently by a mass flowmeter and a controller. The individual reactor pressure was controlled independently by a pressure control system including a pressure transducer and a control valve. The effluents of both reactors were routed to a scrubber containing 10% KOH solution to neutralize HCl generated in the process. Samples were taken periodically using a sample bag containing certain amount of de-ionized $H_2O$ from the sample port before the crude product reached the scrubber solution.

In one reactor, the un-distilled 244bb crude, which had the same composition as 244bb crude of Example 2 (see Table 2 for its composition) was used as the starting material.

In the other reactor, the distilled 244bb, which was the 244bb distillate from Example 2 (see Table 2 for its composition) was used as the starting material.

Figure 5:
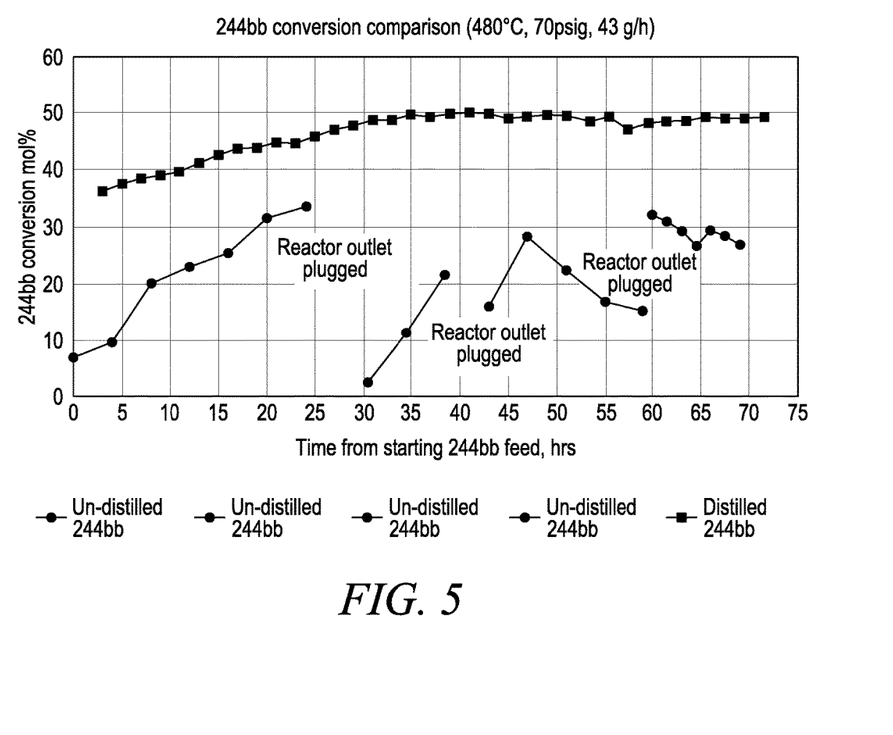
FIG. 5 is a chart illustrating 244bb conversion data with two different 244bb feed materials.

Both reactors were running at same reaction conditions (480° C., 70 psig with 43 g/h of feed rate equivalent to 80 seconds of residence time), with 244bb conversion data shown in FIG. 5.

The reactor with crude 244bb as the starting material experienced significant outlet pluggage after 24 hours of operation. By visual observation, the reactor outlet was packed with tar-like black solids. The outlet was plugged again after tar-like material was cleared and 8 hours after the reaction was restarted. The third pluggage was observed after tar-like material was cleared and 16 hours after the reaction was restarted. 244bb conversion was very low and unstable using crude 244bb as the starting material. On the other hand, the reactor run with distilled 244bb as the staring material was able to maintain high and stable activity without any operation issues after the induction period. In addition, with the crude 244bb as the starting material, the normalized HFO-1243zf and 1140 concentrations in the reactor effluent were 159 ppm and 247 ppm, respectively. With the distilled 244bb as the starting material, the average normalized HFO-1243zf and HCC-1140 concentrations in the reactor effluent were 75 ppm and 30 ppm, respectively.

Example 4

The distilled 244bb as described in Example 2 was fed into one of the reactors as described in Example 3 at 465° C., 70 psig with 21.5 g/h feed rate (equivalent to 164 seconds of residence time). By GC analysis, the average normalized HFO-1243zf and HCC-1140 concentrations in the reactor effluent were 56 ppm and 38 ppm, respectively.

Example 5

The distilled 244bb as described in Example 2 was fed into one of the reactors as described in Example 3 at 465° C., 70 psig with 43 g/h feed rate (equivalent to 82 seconds of residence time). By GC analysis, the average normalized HFO-1243zf and HCC-1140 concentrations in the reactor effluent were 71 ppm and 27 ppm, respectively.

Example 6

The distilled 244bb as described in Example 2 was fed into one of the reactors as described in Example 3 at 480° C., 70 psig with 21.5 g/h feed rate (equivalent to 161 seconds of residence time). By GC analysis, the average normalized HFO-1243zf and HCC-1140 concentrations in the reactor effluent were 59 ppm and 98 ppm, respectively.

Example 7

The distilled 244bb as described in Example 2 was fed into one of the reactors as described above in Example 3 at 480° C., 58 psig with 43 g/h feed rate (equivalent to 69 seconds of residence time). By GC analysis, the average normalized HFO-1243zf and HCC-1140 concentrations in the reactor effluent were 68 ppm and 21 ppm, respectively.

Example 8

Under the same reaction conditions as described in Example 3, a starting material containing 27 ppm HFC-253fb, 98.46% 244bb and 0.84% 1233xf was fed into one of the reactors. By GC analysis, the average normalized HFO-1243zf and HCC-1140 concentrations in the reactor effluent were 63 ppm and 42 ppm, respectively.

Example 9

Under the same reaction conditions as described in Example 3, a starting material containing 41 ppm HFC-253fb, 98.42% 244bb and 0.85% 1233xf was fed into one of the reactors. By GC analysis, the average normalized HFO-1243zf and HCC-1140 concentrations in the reactor effluent were 78 ppm and 44 ppm, respectively.

Example 10

Under the same reaction conditions as described in Example 3, a starting material containing 53 ppm HFC-253fb, 97.32% 244bb and 1.47% 1233xf was fed into one of the reactors. By GC analysis, the average normalized HFO-1243zf and HCC-1140 concentrations in the reactor effluent were 120 ppm and 165 ppm, respectively.

Example 11

Under the same reaction conditions as described in Example 3, a starting material from the plant (after Heavies were removed by distillation) containing 14 ppm HFC-253fb, 98.59% 244bb and 1.03% 1233xf was fed into one of the reactors. By GC analysis, the average normalized HFO-1243zf and HCC-1140 concentrations in the reactor effluent were 48 ppm and 23 ppm, respectively.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of manufacturing 2,3,3,3-tetrafluoropropene (HFO-1234yf) comprising:
   providing a feed comprising 2-chloro-1,1,1,2-tetrafluoropropane (HCFC-244bb) and 1-chloro-3,3,3-trifluoropropane (HCFC-253fb);
   removing the HCFC-253fb from the feed until the feed contains less than 200 ppm of the HCFC-253fb; and
   dehydrochlorinating the HCFC-244bb in the feed to form a product stream containing HFO-1234yf.

2. The method of claim 1, wherein the removing step comprises at least one of distillation, partial vaporization, partial condensing, or combinations thereof.

3. The method of claim 2, wherein the removing step comprises continuous distillation.

4. The method of claim 1, wherein the removing the HCFC-253fb from the feed is performed until the feed contains less than 100 ppm of the HCFC-253fb.

5. The method of claim 4, wherein the removing the HCFC-253fb from the feed is performed until the feed contains less than 50 ppm of the HCFC-253fb.

6. A method of manufacturing 2,3,3,3-tetrafluoropropene (HFO-1234yf) comprising:
   providing a feed comprising 2-chloro-1,1,1,2-tetrafluoropropane (HCFC-244bb), HF, and 1-chloro-3,3,3-trifluoropropane (HCFC-253fb);
   separating the HF and the HCFC-253fb; and dehydrochlorinating the HCFC-244bb in the feed to form a product stream containing HFO-1234yf.

7. The method of claim 6, wherein the separating step comprises distillation.

8. The method of claim 7, wherein the distillation is multistage distillation.

9. The method of claim 7, wherein at least a portion of the HCFC-253fb is separated by taking a side draw from a distillation column.

10. The method of claim 7, wherein the distillation is continuous distillation.

11. The method of claim 6, wherein the separating comprises at least one of decanting, centrifuging, liquid-liquid extraction, distilling, flash distilling, or combinations thereof.

12. The method of claim 6, wherein the separating step comprises forming an azeotrope in a distillation column.

13. The method of claim 6, further comprising, after dehydrochlorination, separating and recycling unreacted HCFC-244bb.

14. A method of manufacturing 2,3,3,3-tetrafluoropropene (HFO-1234yf) comprising:

providing a feed comprising 2-chloro-1,1,1,2-tetrafluoropropane (HCFC-244bb) and 1-chloro-3,3,3-trifluoropropane (HCFC-253fb);
dehydrochlorinating the HCFC-244bb in the feed to form a product stream containing HFO-1234yf; and
controlling the formation of vinyl chloride (1140), 3,3,3-trifluoropropene (HFO-1243zf), or combinations thereof at or below a predetermined threshold, wherein the controlling the formation 1140, HFO-1243zf, or combinations thereof includes removal of HCFC-253fb prior to the dehydrochlorinating step.

15. The method of claim 14, wherein the predetermined threshold is about 300 ppm.

16. The method of claim 14, wherein the removal of HCFC-253fb is performed until the feed has less than 200 ppm of HCFC-253fb.

17. The method of claim 14, wherein the formation of vinyl chloride (1140) is controlled below 200 ppm.

18. The method of claim 14, wherein the formation of 3,3,3-trifluoropropene (HFO-1243zf) is controlled below 200 ppm.

19. The method of claim 2, wherein the distillation comprises removal of the HCFC-244bb from a side-draw.

* * * * *